(12) United States Patent
Matsuda et al.

(10) Patent No.: US 6,372,915 B1
(45) Date of Patent: Apr. 16, 2002

(54) PROCESS FOR PRODUCING OXAZOLE COMPOUND

(75) Inventors: Koji Matsuda; Katsuyoshi Hara; Minoru Akamatsu, all of Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/786,267

(22) PCT Filed: Sep. 1, 1999

(86) PCT No.: PCT/JP99/04753

§ 371 Date: Mar. 2, 2001

§ 102(e) Date: Mar. 2, 2001

(87) PCT Pub. No.: WO00/14078

PCT Pub. Date: Mar. 16, 2000

(30) Foreign Application Priority Data

Sep. 3, 1998 (JP) .............................. 10-249621

(51) Int. Cl.$^7$ .............................. C07D 263/32

(52) U.S. Cl. .................................... 548/235

(58) Field of Search ........................ 548/235

(56) References Cited

FOREIGN PATENT DOCUMENTS

| | | |
|---|---|---|
| EP | 0 745 596 | 12/1996 |
| JP | 9 52882 | 2/1997 |
| WO | WO 96/19463 | 6/1996 |

OTHER PUBLICATIONS

"Kagaku Daijiten 1, Pocket Edition," Ed. Kyoritsu Shuppan K.K., Mar. 30, 1960, p. 1049.
"Kagaku Daijiten 5, Pocket Edition," Ed. Kyoritsu Shuppan K.K., Apr. 15, 1961, p. 226.

*Primary Examiner*—Laura L. Stockton
(74) *Attorney, Agent, or Firm*—Foley & Lardner

(57) ABSTRACT

The present invention relates to a method for producing a compound of the formula [7]

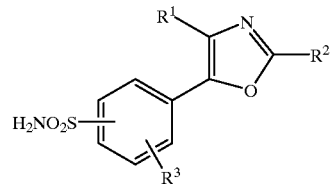

[7]

wherein $R^1$ is an optionally substituted cycloalkyl group, an optionally substituted aryl group or an optionally substituted heterocyclic group, $R^2$ is a lower alkyl or a halogenated lower alkyl and $R^3$ is a halogen atom or a hydrogen atom. The method of the present invention includes reacting compound [1] with thionyl chloride to give compound [2] and obtaining the objective compound [7] at a high yield via intermediate [5], and is utilizable for industrial production.

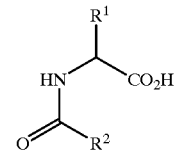

[1]

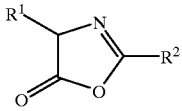

[2]

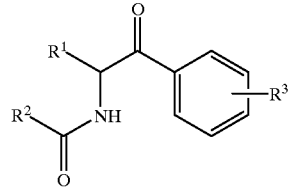

[5]

6 Claims, No Drawings

PROCESS FOR PRODUCING OXAZOLE COMPOUND

This application is a 371 of PCT/JP99/04753 filed Sep. 1, 1999.

TECHNICAL FIELD

The present invention relates to a novel production method of an oxazole compound of the formula [7] having a selective inhibitory action on cyclooxygenase-2 (COX-2)

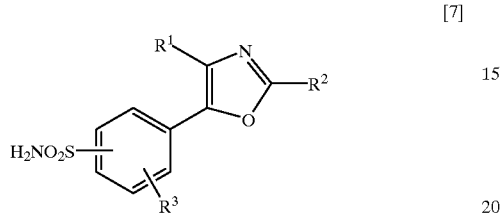

[7]

wherein $R^1$ is an optionally substituted cycloalkyl group, an optionally substituted aryl group or an optionally substituted heterocyclic group, $R^2$ is a lower alkyl or a halogenated lower alkyl, and $R^3$ is a halogen atom or a hydrogen atom. The present invention also relates to a method for producing intermediates for the production of a compound of the above-mentioned formula [7].

BACKGROUND ART

The above-mentioned compound [7], which selectively inhibits cyclooxygenase-2 (COX-2), is useful as, for example, an antiinfammatory agent. The production method of compound [7] has been already disclosed in the specification of WO96/ 19463.

However, the conventional production methods require many treatment steps and the yields of the final product and intermediates therefor are not entirely satisfactory. In addition, the reagent, solvent and the like to be used in each step suffice for use only at laboratory levels and many of them are problematically impractical and cannot be used in industrial production.

DISCLOSURE OF THE INVENTION

The present inventors have studied respective steps in detail and improved them. To be specific, they considered the production method (hereinafter to be referred to as method A) disclosed in WO96/ 19463, which is most similar to the present invention.

According to the method A, compound [7'], which is one of the objective compounds of the present invention, is produced by the following Steps 1–4.

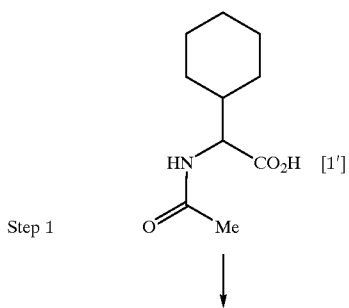

Step 1

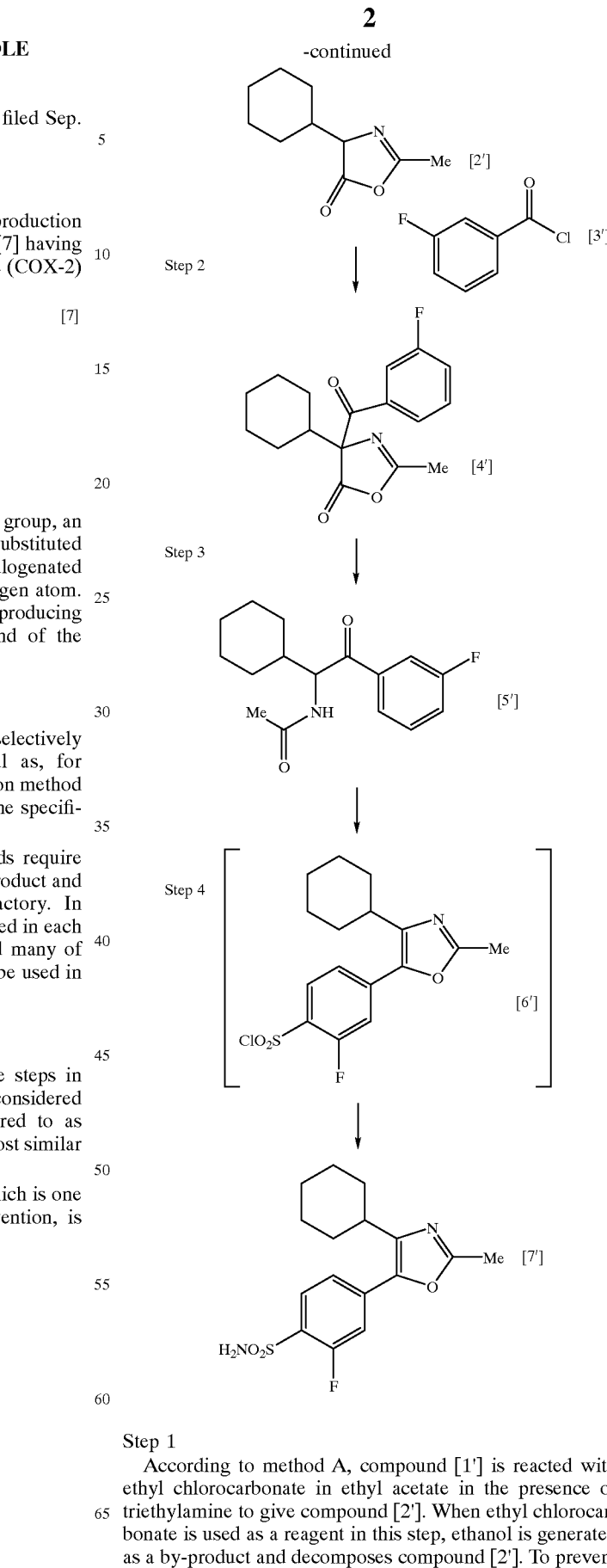

Step 1

According to method A, compound [1'] is reacted with ethyl chlorocarbonate in ethyl acetate in the presence of triethylamine to give compound [2']. When ethyl chlorocarbonate is used as a reagent in this step, ethanol is generated as a by-product and decomposes compound [2']. To prevent this, a complicated post-treatment such as desalting filtration and concentration is needed after the main reaction, cyclization. Thus, method A is associated with a complicated post-treatment and lower yield of compound [2'] due to the generation of the by-product. The present inventors considered using economical thionyl chloride instead of ethyl chlorocarbonate to solve this problem. As a result, they have found that the use of thionyl chloride obliterates the above-mentioned complicated post-treatment and generation of the by-product, which has led to an improvement in the yield. It has been also found that the unstable compound [2'] can be used in the next step without isolation or purification. These improvements have achieved an increase in the yield.

Step 2

In method A, compound [2'] is reacted with compound [3'] in a tetrahydrofuran suspension of magnesium chloride in the presence of triethylamine to give compound [4']. Tetrahydrofuran used as a reagent and solvent in this step is not a most suitable solvent in terms of cost, when industrially used in a large amount. Thus, the present inventors have studied solvents to find out a solvent economical and suitable for industrial production, as well as from the aspect of an improved yield. Consequently, they have found that ethyl acetate, which is recited in the specification of WO96/19463 as a general example but is not specifically disclosed as an example, can be used to conduct this reaction similarly. This change of solvent offers merits of not only low cost but omission of concentration of the reaction solvent before extraction in the next step (Step 3). This has offered a simultaneous resolution to the problems of reduction of cost and increase in yield. In addition, they have found that the unstable compound [4'] can be used in the next step without isolation or purification. These improvements resulted in an increased yield.

Step 3

In method A, hydrochloric acid is added to compound [4'] in trahydrofuran to allow hydrolysis and decarboxylation. Subsequently, compound [5'] is obtained through post-treatment of concentration of the reaction solvent (tetrahydrofuran), extraction, concentration of the extraction solvent and the like. The present inventors changed tetrahydrofuran, the solvent used in the previous step (Step 2), to ethyl acetate and conducted Step 3 in ethyl acetate, whereby they have succeeded in omitting a step for concentration of tetrahydrofuran before extraction. This has led to the improved yield of compound [5'].

When compared in the yields of Compound [5'] from compound [1'], it was 67.7% by method A but 84.7% by the present invention, thus achieving a 17% increase in the yield.

Step 4

In method A, compound [5'] is reacted with chlorosulfonic acid in chloroform to give compound [6']. Further, by reacting this compound with aqueous ammonia in tetrahydrofuran without isolation, objective compound [7'] is obtained. The solvent used here is chloroform, which has strong toxicity and is problematic for industrial use. The present inventors have overcome this problem by the use of a method generally exemplified in the specification of WO96/19463 but not specifically shown as an example. Surprisingly, the reaction was found to proceed as smoothly as when chloroform was used, even without a solvent.

The method A is not satisfactory in terms of the yield of the objective compound [7']. According to method A, compound [7'] is obtained through a post-treatment of concentration of the reaction solvent (tetrahydrofuran), extraction, concentration of the extraction solvent and the like. Like Step 2, the present inventors changed the solvent for amidation from tetrahydrofuran to ethyl acetate to omit concentration of tetrahydrofuran before extraction.

This has led to the elimination of problems associated with the prior art technique, and the yield of compound [7'] from compound [5'] was increased by about 5% from 77.2% to 82.0%.

As mentioned above, the present inventors studied the problems in each step in detail with the aim of improving the yield of the objective compound and establishing the method capable of affording industrial production, and they have found that the use of the above-mentioned solvent, reagent and the like in each step results in the production of the objective compound at a high yield and also an industrially practical production method, which resulted in the completion of the present invention.

Accordingly, the present invention provides the following (1) to (9).

(1) A production method of an oxazole compound of the formula [7]

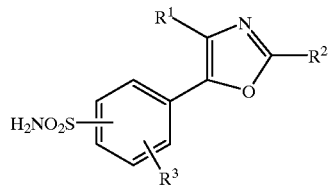

wherein $R^1$ is an optionally substituted cycloalkyl group, an optionally substituted aryl group or an optionally substituted heterocyclic group, $R^2$ is a lower alkyl or a halogenated lower alkyl and $R^3$ is a halogen atom or a hydrogen atom, comprising reacting a compound of the formula [1]

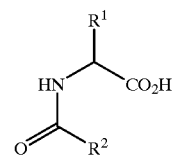

wherein $R^1$ and $R^2$ are as defined above, with thionyl chloride in an inert solvent in the presence of a base, to give an oxazolone compound of the formula [2]

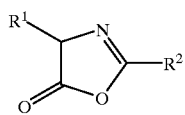

wherein $R^1$ and $R^2$ are as defined above, subsequently reacting this compound with a compound of the formula [3]

wherein R³ is as defined above and X is a halogen atom, in ethyl acetate in the presence of a magnesium salt and a base to give a compound of the formula [4]

[4]

wherein R¹, R² and R³ are as defined above, subjecting this compound to hydrolysis and decarboxylation with an acid to give a compound of the formula [5]

[5]

wherein R¹, R² and R³ are as defined above, subjecting this compound to cyclization and sulfonation with a sulfonating agent and chlorination with thionyl chloride to give a compound of the formula [6]

[6]

wherein R¹, R² and R³ are as defined above, and subjecting this compound to amidation in ethyl acetate with aqueous ammonia (2) The method of (1) wherein $R^1$ is a cycloalkyl, $R^2$ is a lower alkyl, and $R^3$ is a halogen atom.
(3) The method of (1) wherein $R^1$ is a cyclohexyl, $R^2$ is a methyl, and $R^3$ is a fluorine atom.
(4) A production method of an acetophenone compound of the formula [5]

[5]

wherein $R^1$ is an optionally substituted cycloalkyl group, an optionally substituted aryl group or an optionally substituted heterocyclic group, $R^2$ is a lower alkyl or a halogenated lower alkyl and R3 is a halogen atom or a hydrogen atom, comprising reacting a compound of the formula [1]

[1]

wherein $R^1$ and $R^2$ are as defined above, with thionyl chloride in an inert solvent in the presence of a base to give an oxazolone compound of the formula [2]

[2]

wherein $R^1$ and $R^2$ are as defined above, sequentially reacting this compound with a compound of the formula [3]

[3]

wherein R³ is as defined above and X is a halogen atom, in ethyl acetate in the presence of a magnesium salt and a base to give a compound of the formula [4]

[4]

wherein R¹, R² and R³ are as defined above, and subjecting this compound to hydrolysis and decarboxylation with an acid.
(5) The method of (4) wherein $R^1$ is a cycloalkyl, $R^2$ is a lower alkyl, and $R^3$ is a halogen atom.

(6) The method of (4) wherein $R^1$ is a cyclohexyl, $R^2$ is a methyl, and $R^3$ is a fluorine atom.

(7) A production method of an oxazole compound of the formula [7]

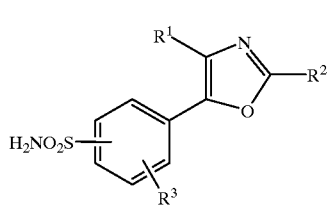

[7]

wherein $R^1$ is an optionally substituted cycloalkyl group, an optionally substituted aryl group or an optionally substituted heterocyclic group, $R^2$ is a lower alkyl or a halogenated lower alkyl and $R^3$ is a halogen atom or a hydrogen atom, comprising subjecting a compound of the formula [5]

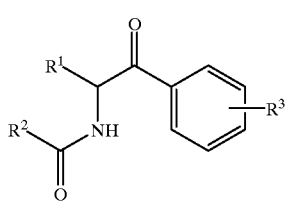

[5]

wherein $R^1$, $R^2$ and $R^3$ are as defined above, to cyclization and sulfonation with a sulfonating agent, and chlorination with thionyl chloride to give a compound of the formula [6]

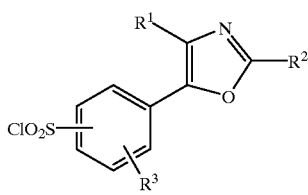

[6]

wherein $R^1$, $R^2$ and $R^3$ are as defined above, and then subjecting this compound to amidation in ethyl acetate with aqueous ammonia.

(8) The method of (7) wherein $R^1$ is a cycloalkyl, $R^2$ is a lower alkyl, and R3 is a halogen atom.

(9) The method of (7) wherein $R^1$ is a cyclohexyl, $R^2$ is a methyl, and $R^3$ is a fluorine atom.

Each substituent used in the present specification are defined as follows.

The cycloalkyl group is that having 3 to 8 carbon atoms, which is specifically exemplified by cyclopropyl, cyclobutyl, cyclopentyl, cyclohexyl, cycloheptyl and cyclooctyl. Preferred is cycloalkyl group having 5 to 7 carbon atoms. Specific examples thereof include cyclopentyl, cyclohexyl and cycloheptyl, where particularly preferred is cyclohexyl.

The heterocyclic group is a 5- or 6-membered aromatic heterocycle, saturated heterocycle, unsaturated heterocycle, or condensed heterocycle wherein such heterocycle and a benzene ring or cyclohexane ring are condensed, which has, as an atom constituting the ring, 1 to 3 hetero atoms selected from nitrogen atom, oxygen atom and sulfur atom, besides carbon atom. Specific examples thereof include thienyl, furyl, pyrrolyl, imnidazolyl, pyrazolyl, thiazolyl, isothiazolyl, oxazolyl, isoxazolyl, morpholino, morpholinyl, piperazinyl, piperidyl, pyranyl, thiopyranyl, pyridyl, benzothienyl, benzofuranyl, indolyl, 4,5,6,7-tetrahydroindolyl, 4,5,6,7-tetrahydrobenzothienyl, 4,5,6,7-tetrahydrobenzofuranyl and the like. Preferred are thienyl, furyl, pyrrolyl, morpholino, morpholinyl, piperazinyl and piperidyl, and particularly preferred is thienyl.

The aryl group is, for example, phenyl, naphthyl, biphenylyl and the like, with preference given to phenyl.

The "optionally substituted" means that the group may be substituted by 1 to 3 substituents which may be the same or different. The position of the substituent is optional and subject to no particular limitation. Specific examples thereof include lower alkyl such as methyl, ethyl, propyl, isopropyl, butyl, tert-butyl and the like; hydroxy; lower alkoxy such as methoxy, ethoxy, propoxy, butoxy and the like; halogen atom such as fluorine, chlorine, bromine and the like; nitro; cyano; acyl (e.g., formyl, or lower alkylcarbonyl such as acetyl, propionyl and the like); acyloxy such as formyloxy, acetyloxy, propionyloxy and the like (acyl moiety being as defined above); mercapto; lower alkylthio such as methylthio, ethylthio, propylthio, butylthio, isobutylthio and the like; amino; lower alkylamino such as methylamino, ethylamino, propylamino, butylamino and the like; di(lower)alkylamino such as dimethylamino, diethylamino, dipropylamino, dibutylamino and the like; carboxy; lower alkoxycarbonyl such as methoxycarbonyl, ethoxycarbonyl, propoxycarbonyl and the like; amido; trifluoromethyl; lower alkylsufonyl such as methylsulfonyl, ethylsulfonyl and the like; aminosulfonyl; lower cycloalkyl such as cyclopentyl, cyclohexyl and the like; phenyl; and acylamino such as acetamido, propionamido and the like (acyl moiety being as defined above), with preference given to hydroxy, lower alkyl, lower alkoxy, mercapto, lower allkylthio, halogen atom, tifluoromethyl, lower alkylcarbonyl, lower alkoxycarbonyl and acylamino. As used herein, by lower is meant that the number of carbon atoms is preferably 1 to 6, more preferably 1 to 4.

More specifically, the "optionally substituted aryl group" means aryl group, particularly phenyl group optionally substituted by halogen atom, hydroxy, lower alkyl, lower alkoxy, lower alkylsulfonyl, aminosulfonyl and the like. Specific examples thereof include phenyl, fluorophenyl, methylphenyl, methoxyphenyl, methylsulfonylphenyl, arninosulfonylphenyl and the like, preferably phenyl and 4-fluorophenyl.

The "optionally substituted heterocyclic group" is heterocyclic group optionally substituted by halogen atom, hydroxy, lower alkyl, lower alkoxy, lower alkylsulfonyl, aminosulfonyl and the like, with preference given to thienyl, furyl, 5-methylthienyl and 5-chlorothienyl.

The "optionally substituted cycloalkyl group" is cycloalkyl group optionally substituted by halogen atom, hydroxy, lower alkyl, lower alkoxy, lower alkylsulfonyl, aminosulfonyl and the like, with preference given to cyclopropyl, cyclobutyl, cyclopentyl, cyclohexyl, 4methylcyclohexyl, 4-hydroxycyclohexyl, 4-fluorocyclohexyl and the like, particularly preferably cyclohexyl.

The "lower aLkyl" is linear or branched alkyl having 1 to 6 carbon atoms, such as methyl, ethyl, propyl, isopropyl, butyl, isobutyl, sec-butyl, tert-butyl, pentyl, isopentyl, neopentyl, 1-ethylpropyl, tert-pentyl, hexyl and the like, which is preferably methyl.

The "halogen atom" means chlorine atom, bromine atom, fluorine atom and the like, with preference given to chlorine atom and fluorine atom. At R³, it is preferably fluorine atom and at X, it is preferably chlorine atom.

The "halogenated lower alkyl" is the above-mentioned lower alkyl substituted by the above-mentioned halogen atom. Specific examples thereof include fluoromethyl, chloromethyl, bromomethyl, iodomethyl, difluoromethyl, dichloromethyl, trifluoromethyl, trichloromethyl, fluoroethyl, chloroethyl, difluoroethyl, dichloroethyl, trifluoroethyl, trichloroethyl, tetrachloroethyl, pentafluoroethyl, fluoropropyl and the like, with preference given to fluoromethyl, chloromethyl, dichloromethyl, difluoromethyl, trichloromethyl and trifluoromethyl.

The "inert solvent" means ethyl acetate, tetrahydrofuran, toluene, dichloromethane and the like, preferably ethyl acetate.

The "base" is a tertiary amine such as triethylamine, pyridine, N-methylmorpholine and the like; secondary amine such as diethylamine, diisopropylamine and the like; and inorganic base such as potassium carbonate, sodium carbonate and the like, with preference given to tertiary amine, which is more preferably triethylarine.

The "magnesium salt" means anhydrous magnesium chloride, anhydrous magnesium bromide and the like, which is preferably anhydrous magnesium chloride.

The "acid" means hydrochloric acid, oxalic acid, diluted sulfuric acid, phosphoric acid and the like, which is preferably hydrochloric acid.

The "sulfonating agent" means chlorosulfonic acid, anhydrous sulfuric acid, concentrated sulfuric acid, fuming sulfuric acid and the like, which is preferably chlorosulfonic acid.

The production method of oxazole compound of the formula [7] is described in detail in the following.

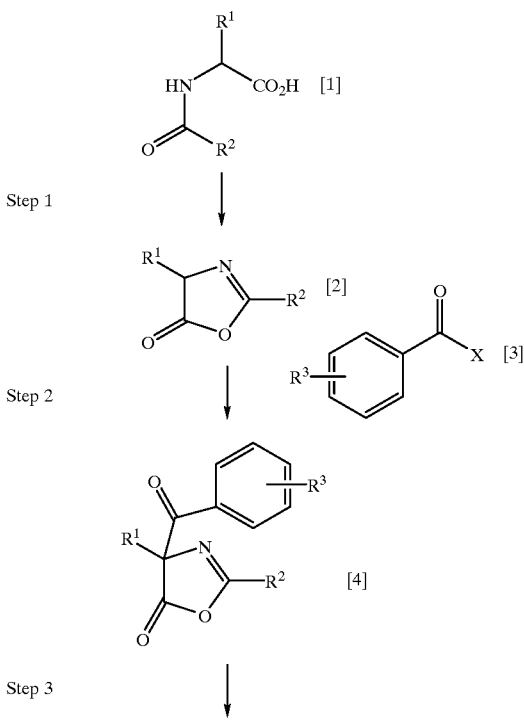

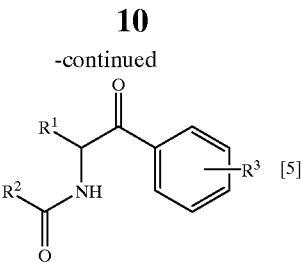

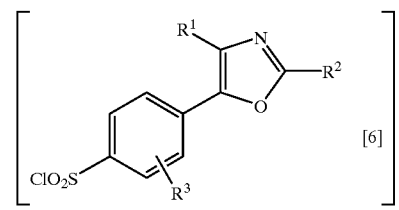

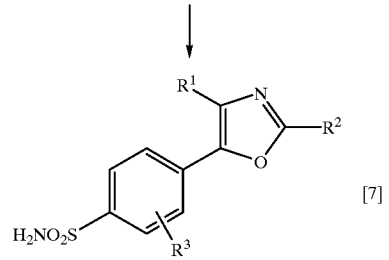

wherein $R^1$, $R^2$, $R^3$ and X are as defined above.

General Production Method

Step 1

Compound [1] is reacted with thionyl chloride in an inert solvent in the presence of a base to give compound [2].

The inert solvent to be used for the reaction is ethyl acetate, tetrahydrofuran, toluene, dichloromethane and the like, which is preferably ethyl acetate.

Specific examples of the base include tertiary amine such as triethylamine, pyridine, N-methylmorpholine and the like; secondary amine such as diethylamine, diisopropylamine and the like; and inorganic base such as potassium carbonate, sodium carbonate and the like, with preference given to tertiary amine, which is more preferably triethylamine.

The reaction temperature is −20° C. to 20° C., preferably −10° C. to 0° C.

The reaction time is 0.5–10 hours, preferably 0.5–2 hours.

When this reaction is carried out, the reaction preferably proceeds under an inert gas atmosphere (e.g., nitrogen) to prevent reduction in the yield due to contamination with water.

The obtained compound [2] can be used in the next reaction without isolation.

Step 2

Compound [2] is reacted with compound [3] in ethyl acetate in the presence of a magnesium salt and a base to give compound [4].

As the magnesium salt, anhydrous magnesium chloride, anhydrous magnesium bromide and the like, preferably anhydrous magnesium chloride, can be used.

Examples of the base include tertiary amine such as triethylamine, pyridine, N-methylmorpholine and the like; secondary amine such as diethylamine, diisopropylamine and the like; and inorganic base such as potassium carbonate, sodium carbonate and the like, with preference given to tertiary amine, which is more preferably triethylamine.

The reaction temperature is −20° C. to 20° C., preferably 0° C. to 10° C.

The reaction time is 1–20 hours, preferably 6–15 hours.

This reaction is desirably carried out under an inert gas atmosphere, such as nitrogen as in Step 1, to prevent reduction in the yield due to contamination with water.

In this step, ether such as tetrahydrofuran, diethyl ether and the like, preferably tetrahydrofuran, is used as a reagent, which ensures smooth progress of the reaction. Ether is added in 2–5 equivalents, preferably 2 equivalents, relative to compound [2].

The obtained compound [4] can be used in the next reaction without isolation.

Step 3

Compound [4] is subjected to hydrolysis and decarboxylation with an acid to give compound [5].

This reaction preferably proceeds in a mixed solvent of ethyl acetate and water.

The acid to be used is exemplified by hydrochloric acid, oxalic acid, diluted sulfuric acid, phosphoric acid and the like, which is preferably hydrochloric acid.

The reaction temperature is −20° C. to 100° C., preferably 35° C. to 45° C.

The reaction time is 1–20 hours, preferably 1–3 hours.

Step 4

Compound [5] is subjected to cyclization and sulfonation with a sulfonating agent, and chlorination with thionyl chloride to give compound [6]. Sequentially, the product is, without isolation, reacted with aqueous ammonia in ethyl acetate to give the objective compound [7].

The reactions of cyclization and sulfonation are preferably carried out without solvent.

The sulfonating agent to be used is exemplified by chlorosulfonic acid, anhydrous sulfuric acid, concentrated sulfuric acid, fuming sulfuric acid and the like, which is preferably chlorosulfonic acid.

The temperature of the reaction to obtain compound [6] from compound [5] is 0° C.–200° C., preferably 75° C.–95° C. The time of the reaction of cyclization and sulfonation is 1–10 hours, preferably 2–5 hours. The reaction time of chlorination is 0.5–10 hours, preferably 0.5–5 hours.

In the reaction to obtain compound [6] from compound [5], the reaction is desirably carried out under an inert gas atmosphere, such as nitrogen as in Step 1, to prevent reduction in the yield due to contamination with water.

The temperature of the reaction to obtain compound [7] from compound [6] is −20° C. to 200° C., preferably −10° C. to 10° C. The reaction time is 1–24 hours, preferably 1–3 hours.

EXAMPLES

Example 1

2-N-Acetylamino-2-cyclohexyl-3'-fluoroacetophenone (production method of compound [5] wherein $R^1$=cyclohexyl, $R^2$=methyl, $R^3$=3-fluoro)

DLN-Acetyl-2-cyclohexylglycine (60.0 g) was suspended in ethyl acetate (420 mL) under a nitrogen atmosphere, and triethylamine (45.7 g) was added thereto for dissolution. Thionyl chloride (37.6 g), and then triethylamine (106.6 g) were added dropwise under cooling in such a manner that the inside temperature did not exceed 0° C. After the completion of the dropwise addition, the mixture was stirred at −10° C. to 0° C. for not less than 30 minutes to give a mixture of 4-cyclohexyl-2-methyl-5-oxazolone in ethyl acetate.

To this mixture of 4-cyclohexyl-2-methyl-5-oxazolone in ethyl acetate was added, under a nitrogen atmosphere, a mixture of ethyl acetate (120 mL) and tetrahydrofuran (43.4 g) added with anhydrous magnesium chloride (28.7 g), and the mixture was stirred at 0° C.–10° C. for 1 hour or more. Thereto was added dropwise 3-fluorobenzoyl chloride (47.7 g) at 0° C.–10° C. and the mixture was stirred at 0° C.–10° C. for 6 hours or more to give a mixture of 4-cyclohexyl-4-(3-fluorobenzoyl)-2-methyl-5-oxazolone and ethyl acetate.

To this mixture of 4-cyclohexyl-4-(3-fluorobenzoyl)-2-methyl-5-oxazolone in ethyl acetate were added dropwise 35% hydrochloric acid (72.1 g) and water (173 mL) in such a manner that the inside temperature did not exceed 45° C. This reaction mixture was stirred at 35° C.–45° C. for one hour or more, cooled to 10° C.–30° C. and allowed to stand still for separation of layers, and the aqueous layer was removed. The obtained organic layer was washed with water (420 mL), 20% aqueous potassium carbonate solution (420 g), and 10% brine (420 g). The organic layer obtained by standing still was concentrated to 198 g and the residue was dissolved by heating, which was followed by addition of heptane (212 mL). The inside temperature was cooled to 55° C.–65° C., matured for crystallization at 55° C.–65° C. for 1 hour or more, cooled to not more than −10° C. and matured for crystazation at not more than −10° C. for one or more hours. This crystal mixture was filtered and the crystals collected by filtration were washed with a mixture of ethyl acetate (54 mL) and heptane (162 mL) cooled to −10° C. The crystals were dried under reduced pressure to give the title compound (compound [5]; 70.7 g, yield 84.7%) as slightly yellow white crystals.

m.p.: 116–118° C.; $^1$H-NMR (300 MHz, CDCl$_3$, TMS): δ0.9–1.3 (5H, m), 1.5 (1H, m), 1.6–1.9 (4H, m), 2.07 (3H, s), 5.52 (1H, dd ), 6.27 (1H, br-d), 7.31 (1H, td), 7.49 (1H, td), 7.67 (1H, td), 7.79 (1H, br-d) IR (KBr): 3282, 2920, 1681, 1637, 1588, 1297 cm$^{-1}$; MS (FAB+): 278 (MH$^+$).

Example 2

5-(4-Aminosulfonyl-3-fluorophenyl)-4-cyclohexyl-2-methyloxazole (production method of compound [7] wherein $R^1$=cyclohexyl, $R^2$=methyl, $R^3$=3-fluoro)

2-N-Acetylamino-2-cyclohexyl-3'-fluoroacetophenone (60.0 g) was cast portionwise into chlorosulfonic acid (126.1 g) under a nitrogen atmosphere in such a manner that the inside temperature did not exceed 20° C. The mixture was stirred at an inside temperature of 75° C.–95° C. for 2 hours or more and thionyl chloride (77.2 g) was added dropwise at 75° C.–95° C., which was followed by stirring at 75° C.–95° C. for 30 minutes or more. The reaction mixture was cooled to not more than 5° C. and ethyl acetate (180 mL) was added dropwise in such a manner that the inside temperature did not exceed 10° C., which was followed by cooling to not more than 5° C. This reaction mixture was added dropwise to a mixture of cooled ethyl acetate-water (120 mL–480 mL; not more than 5° C.) in such a manner that the inside temperature did not exceed 10° C. The container used for the dropwise addition was washed with ethyl acetate (60 mL) and water (60 mL), and the reaction mixture and washing were combined. The mixture was allowed to stand for separation of layers, and the aqueous layer was removed. The obtained organic layer was washed with water (300 mL) to give a solution of 5-(4-chlorosulfonyl-3-fluorophenyl)-4-cyclohexyl-2-methyloxazole in ethyl acetate.

This solution of 5-(4-chlorosulfonyl-3-fluorophenyl)-4-cyclohexyl-2-methyloxazole in ethyl acetate was cooled to not more than 0° C. and added dropwise to a mixture of 25% aqueous ammonia (73.7 g) and ethyl acetate (180 mL) cooled to not more than 0° C. in advance, in such a manner that the inside temperature did not exceed 10° C. The mixture was stirred at −10° C. to 10° C. for not less than 1 hour. To this reaction mixture was added 25% brine (226 g) and the mixture was allowed to stand for separation of layers, and the aqueous layer was removed. The obtained organic layer was washed with 25% brine (226 g). The ethyl acetate extract obtained by standing was concentrated and the solvent was changed to isopropyl alcohol crystallization solvent. This slurry was dissolved by heating and gradually cooled to 30° C.–50° C. After maturing the crystals at 30° C.–50° C. for not less than 1 hour, the mixture was cooled to not more than 10° C. The crystals were matured at not more than 10° C. for not less than 2 hours. The liquid containing crystals was filtered, and the crystals were washed with isopropyl alcohol (180 mL) cooled to not more than 10° C. and dried under reduced pressure to give the title compound (compound [7]; 60.0 g, yield 82.0%) as white crystals.

m.p.: 166–167° C. $^1$H-NMR (300 MHz, CDCl$_3$, TMS): δ1.3–1.5 (3H, m), 1.7–1.9 (7H, m), 2.51 (3H, s), 2.79 (1H, tt, J=3.7, 11.3 Hz ), 5.19 (2H, br-s), 7.36–7.43 (2H, m), 7.94 (1H, t) IR (KBr) : 3342, 3244, 2932, 1612, 1344, 1168 cm$^{-1}$; MS (FAB+): 339 (MH$^+$);

INDUSTRIAL APPLICABILITY

As is evident from the foregoing, the present invention can produce a desired compound [7] that selectively inhibits cyclooxygenase-2 (COX-2) extremely efficiently at high yields as compared to conventional methods. In addition, the production method of the present invention is a highly practical and industrially very useful production method.

This application is based on application no. 249621/1998 filed in japan, the content of which is incorporated hereinto by reference.

What is claimed is:
1. A production method of an oxazole compound of the formula [7]

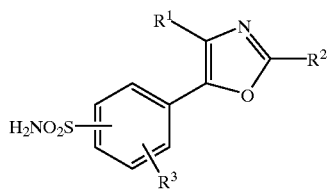

wherein R$^1$ is an optionally substituted cycloalkyl group, an optionally substituted aryl group or an optionally substituted heterocyclic group, R$^2$ is a lower allyl or a halogenated lower alkyl and R$^3$ is a halogen atom or a hydrogen atom, comprising reacting a compound of the formula [1]

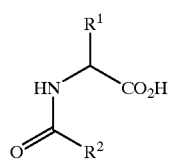

wherein R$^1$ and R$^2$ are as defined above, with thionyl chloride in an inert solvent in the presence of a base, to give an oxazolone compound of the formula [2]

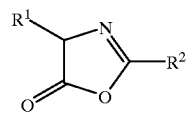

wherein R$^1$ and R$^2$ are as defined above, subsequently reacting this compound with a compound of the formula [3]

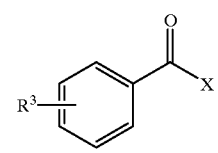

wherein R$^3$ is as defined above and X is a halogen atom, in ethyl acetate in the presence of a magnesium salt and a base to give a compound of the formula [4]

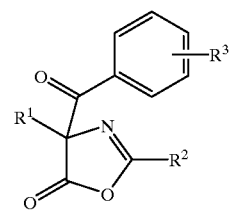

wherein R$^1$, R$^2$ and R$^3$ are as defined above, subjecting this compound to hydrolysis and decarboxylation with an acid to give a compound of the formula [5]

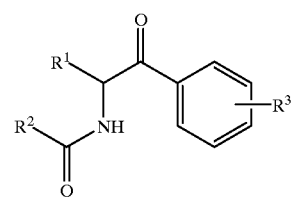

wherein R$^1$, R$^2$ and R$^3$ are as defined above, subjecting this compound to cyclization and sulfonation with a sulfonating agent and chlorination with thionyl chloride to give a compound of the formula [6]

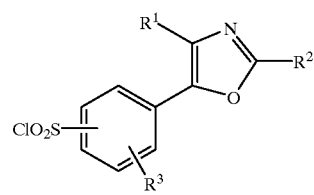

wherein R$^1$, R$^2$ and R$^3$ are as defined above, and subjecting this compound to amidation in ethyl acetate with aqueous ammonia.

2. The method of claim 1, wherein R$^1$ is a cycloalkyl, R$^2$ is a lower alkyl, and R$^3$ is a halogen atom.

3. The method of claim 1, wherein $R^1$ is a cyclohexyl, $R^2$ is a methyl, and $R^3$ is a fluorine atom.

4. A production method of an oxazole compound of the formula [7]

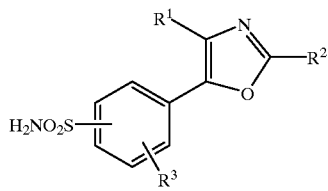

[7]

wherein $R^1$ is an optionally substituted cycloalkyl group, an optionally substituted aryl group or an optionally substituted heterocyclic group, $R^2$ is a lower alkyl or a halogenated lower alkyl and $R^3$ is a halogen atom or a hydrogen atom, comprising subjecting a compound of the formula [5]

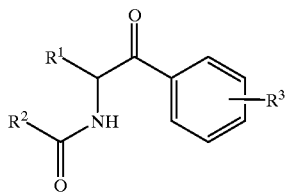

[5]

wherein $R^1$, $R^2$ and $R^3$ are as defined above, to cyclization and sulfonation with a sulfonating agent, and chlorination with thionyl chloride to give a compound of the formula [6]

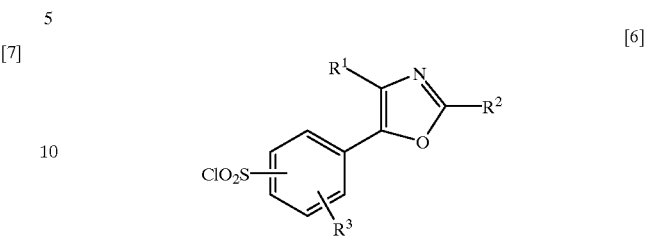

[6]

wherein $R^1$, $R^2$ and $R^3$ are as defined above, and then subjecting this compound to amidation in ethyl acetate with aqueous ammonia.

5. The method of claim 4, wherein $R^1$ is a cycloalkyl, $R^2$ is a lower alkyl, and $R^3$ is a halogen atom.

6. The method of claim 4, wherein $R^1$ is a cyclohexyl, $R^2$ is a methyl, and $R^3$ is a fluorine atom.

* * * * *